(12) United States Patent
Massouda

(10) Patent No.: US 9,644,322 B2
(45) Date of Patent: May 9, 2017

(54) SOLID ARTICLES FROM POLY ALPHA-1,3-GLUCAN AND WOOD PULP

(71) Applicant: E I DU PONT DE NEMOURS AND COMPANY, Wilmington, DE (US)

(72) Inventor: Debora Flanagan Massouda, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/013,279

(22) Filed: Feb. 2, 2016

(65) Prior Publication Data

US 2016/0230348 A1    Aug. 11, 2016

Related U.S. Application Data

(60) Provisional application No. 62/112,916, filed on Feb. 6, 2015.

(51) Int. Cl.
*D21J 3/12* (2006.01)
*C12P 19/04* (2006.01)

(52) U.S. Cl.
CPC .............. *D21J 3/12* (2013.01); *C12P 19/04* (2013.01)

(58) Field of Classification Search
CPC .................................. D21J 3/12; C12P 19/04
USPC ............................................................ 162/175
See application file for complete search history.

(56) References Cited

U.S. PATENT DOCUMENTS

| 7,000,000 | B1 | 2/2006 | Turner et al. |
| 2013/0244287 | A1 | 9/2013 | O'Brien et al. |
| 2013/0244288 | A1 | 9/2013 | O'Brien et al. |
| 2016/0326269 | A1* | 11/2016 | Dennes ...................... C08J 5/18 |
| 2016/0333117 | A1* | 11/2016 | Massouda ........... C08B 37/0009 |
| 2016/0333157 | A1* | 11/2016 | Massouda ........... C08B 37/0009 |

OTHER PUBLICATIONS

Ogawa et al., Fiber Diffraction Methods, 47, pp. 353-362 (1980).
Simpson et al., Microbiology, vol. 141, pp. 1451-1460 (1995).

* cited by examiner

Primary Examiner — Mark Halpern

(57) ABSTRACT

A solid article formed from poly alpha-1,3-glucan and wood pulp is disclosed as are methods for making the solid article. The articles are not water sensitive and are useful for producing strong molded articles from wood pulp.

6 Claims, No Drawings

SOLID ARTICLES FROM POLY ALPHA-1,3-GLUCAN AND WOOD PULP

This application claims the benefit of U.S. Provisional Application No. 62/112,916, filed Feb. 6, 2015, all of which is incorporated herein by reference in its entirety.

FIELD OF DISCLOSURE

This disclosure is in the field of colloidal dispersions. Specifically, this disclosure pertains to using poly alpha-1,3-glucan colloidal dispersions and wood pulp to make solid articles.

BACKGROUND

Driven by a desire to find new structural polysaccharides using enzymatic syntheses or genetic engineering of microorganisms or plant hosts, researchers have discovered polysaccharides that are biodegradable, and that can be made economically from renewable resource-based feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase enzyme isolated from *Streptococcus salivarius* (Simpson et al., *Microbiology* 141:1451-1460, 1995). Films prepared from poly alpha-1,3-glucan tolerate temperatures up to 150° C. and provide an advantage over polymers obtained from beta-1,4-linked polysaccharides (Ogawa et al., *Fiber Differentiation Methods* 47:353-362, 1980).

U.S. Pat. No. 7,000,000 disclosed the preparation of a polysaccharide fiber comprising hexose units, wherein at least 50% of the hexose units within the polymer were linked via alpha-1,3-glycosidic linkages using a *Streptococcus salivarius* gtfJ enzyme. This enzyme utilizes sucrose as a substrate in a polymerization reaction producing poly alpha-1,3-glucan and fructose as end-products (Simpson et al., 1995). The disclosed glucan triacetate polymer formed a liquid crystalline solution when it was dissolved above a critical concentration in a solvent or in a mixture comprising a solvent. From this solution continuous, strong fibers were spun. After regeneration back to glucan, cotton-like fibers, highly suitable for use in textiles, were created and used.

Solid articles can be made from wood pulp. Often, fillers or adhesives are used to hold the wood pulp together. For example, starch could be used but is water sensitive and synthetic binders are used but not very biodegradable.

What is needed is a wood pulp article that is environmentally friendly but not water sensitive.

SUMMARY OF DISCLOSURE

In a first embodiment, the disclosure concerns a solid article comprising: (a) from 50 to 90% by wt. poly alpha-1,3-glucan; and (b) from 10 to 50% by wt. wood pulp.

In a second embodiment, the solid article may further comprise: plasticizers, tougheners and/or fibrillar strengthening agents.

In a third embodiment, the plasticizer is glycerol.

In a fourth embodiment, the solid article can be in the form of sheets, composites, laminates and molded parts.

In a fifth embodiment, the disclosure concerns a process for making a solid article comprising: (a) preparing a poly alpha-1,3-glucan wet cake comprising; (i) heating an enzyme reaction solution comprising an aqueous basic buffered solution of *S. salivarius* gtfJ enzyme, sucrose and, optionally, antimicrobial agent to make a slurry containing poly alpha-1,3-glucan; (ii) filtering the slurry to isolate the poly alpha-1,3-glucan in the form of a wet cake; and (iii) washing the wet cake with water; (b) preparing a mixture from the wet cake with wood pulp, water and, optionally, plasticizers, tougheners and/or fibrillar strengthening agents; (c) homogenizing the mixture; (d) removing at least a portion of the water to form a flowable or malleable material; (e) forming the flowable or malleable material into a shape; and (f) drying the shape to form a solid article.

In a sixth embodiment, the disclosure concerns a solid article prepared from a process comprising: (a) preparing a poly alpha-1,3-glucan wet cake comprising; (i) heating an enzyme reaction solution comprising an aqueous basic buffered solution of *S. salivarius* gtfJ enzyme, sucrose and, optionally, an antimicrobial agent to make a slurry containing poly alpha-1,3-glucan; (ii) filtering the slurry to isolate the poly alpha-1,3-glucan in the form of a wet cake; and (iii) washing the wet cake with water; (b) preparing a mixture from the wet cake with wood pulp, water and, optionally, plasticizers, tougheners and/or fibrillar strengthening agents; (c) homogenizing the mixture; (d) removing at least a portion of the water to form a flowable or malleable material; (e) forming the flowable or malleable material into a shape; and (f) drying the shape to form a solid article.

DETAILED DESCRIPTION OF DISCLOSURE

The disclosures of all patent and non-patent literature cited herein are incorporated herein by reference in their entirety.

As used herein, the term "colloidal dispersion" refers to a heterogeneous system having a dispersed phase and a dispersion medium, i.e., microscopically dispersed insoluble particles are suspended throughout another substance. An example of a colloidal dispersion in water is a hydrocolloid.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages, wherein at least 50% of the glycosidic linkages are alpha-1,3-glycosidic linkages. Poly alpha-1,3-glucan is a type of polysaccharide. The structure of poly alpha-1,3-glucan can be illustrated as follows:

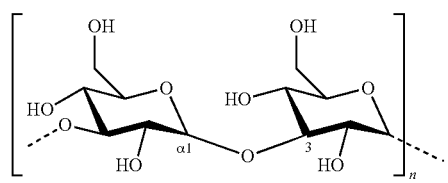

Poly alpha-1,3-glucan can be prepared using chemical methods. Alternatively, it can be prepared by extracting it from various organisms, such as fungi, that produce poly alpha-1,3-glucan. Alternatively still, poly alpha-1,3-glucan can be enzymatically produced from sucrose using one or more glucosyltransferase (gtf) enzymes (e.g., gtfJ), such as described in U.S. Pat. No. 7,000,000, and U.S. Patent Appl. Publ. Nos. 2013/0244288 and 2013/0244287 (all of which are incorporated herein by reference), for example.

The percentage of glycosidic linkages between the glucose monomer units of poly alpha-1,3-glucan used to prepare poly alpha-1,3-glucan compounds herein that are alpha-1,3 is at least 50%, 60%, 70%, 80%, 90%, 95%, 96%, 97%, 98%, 99%, or 100% (or any integer value between 50% and 100%). In such embodiments, accordingly, poly alpha-1,3-glucan has less than 50%, 40%, 30%, 20%, 10%, 5%, 4%, 3%, 2%, 1° A, or 0% (or any integer value between 0% and 50%) of glycosidic linkages that are not alpha-1,3.

The "molecular weight" of the poly alpha-1,3-glucan and poly alpha-1,3-glucan compounds herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements, such as size exclusion chromatography (SEC), or gel permeation chromatography (GPC).

The terms "percent by weight (% by wt.)", "weight percentage (wt %)" and "weight-weight percentage (% w/w)" are used interchangeably herein. Percent by weight refers to the percentage of a material on a mass basis as it is comprised in a composition, mixture or solution.

The term "poly alpha-1,3-glucan slurry" herein refers to an aqueous mixture comprising the components of a glucosyltransferase enzymatic reaction such as poly alpha-1,3-glucan, sucrose, one or more glucosyltransferase enzymes, glucose and fructose.

A poly alpha-1,3-glucan compound disclosed herein can be present in a colloidal dispersion at a weight percentage (wt %) of at least 0.01%, 0.05%, 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.5%, 3.0%, 3.5%, 4.0%, 4.5%, 5%, 6%, 7%, 8%, 9%, 10%, 11%, 12%, 13%, 14% or 15%.

The term "poly alpha-1,3-glucan wet cake" herein refers to poly alpha-1,3-glucan that has been separated from a slurry and washed with water or an aqueous solution. Poly alpha-1,3-glucan is not dried when preparing a wet cake, but some water is removed by filtration. Water remains on the surface of glucan solid particles and trapped between particles. Whereas the glucan colloidal dispersion is a pourable liquid, the wet cake has a soft solid-like consistency. The concentration of glucan in a wet cake can be 10% to 50%.

The term "homogenize" means to mix with high shear to produce a smooth uniform blend.

Particles within glucan dispersions that have never been dried possess the ability to adhere to themselves when dried for the first time. The dried object made by drying a never-dried dispersion resists rehydration but is so brittle that it is not likely to be useful as the primary component in applications that require mechanical integrity. A dry, free-flowing glucan powder can be formed by drying a glucan dispersion or wet cake using process equipment that keeps it moving during drying and/or by grinding the dry dispersion or wet cake. Glucan dry powder can have a water content of between 0% and about 20%. When this powder is reslurried in water and the water is dried, the glucan again becomes a free-flowing powder. This dry powder is not suitable for forming objects where glucan is the primary component.

It has been found that wood pulp also adheres to the glucan particles that have never been dried, and by doing so reduces the brittleness of the final dried object. This is believed to be due to the fibrillar nature of wood pulp.

The first step in creating these toughened glucan objects is to create an intimate blend of wood pulp, the glucan dispersion and any other additive. This blend is generally created by mixing the wood pulp and the glucan dispersion with an excess of water using high shear equipment. At least a portion of the water is then removed, for example, by filtration, from the blend to create a material with a consistency that ranges from pourable or flowable (like a coating) to moldable, malleable or putty-like, depending on how much water is left in. Removing at least a portion of the water means removing at least 10% by weight of the water of the blend, based on the total weight of the water in the blend. In other embodiments, removing at least a portion of the water means removing at least 20% by weight or 30% or 40% or 50% or 60% or 70% or 80% or 90% by weight of the water, based on the total weight of the water in the blend.

The flowable or malleable material can then be pressed into a flat sheet, impregnated into carrier materials or molded into other shapes. The pressed, impregnated or molded article can then be dried to remove greater than or equal to 50% by weight of the water, based on the total weight of the water in the article.

The most brittle of these (unmodified) Comparative Examples breaks before completing even a 10 degree bend, snapping much like a potato chip. The strongest of these Examples is too stiff to bend by hand.

The present disclosure is directed toward a solid article comprising: (a) from 50 to 90% by wt. poly alpha-1,3-glucan; and (b) from 10 to 50% by wt. wood pulp. The solid article may further comprise: plasticizers, tougheners and/or fibrillar strengthening agents. The plasticizer can be glycerol. The solid article can be in the form of sheets, composites, laminates and molded parts.

The present disclosure is further directed toward a process for making a solid article comprising: (a) preparing a poly alpha-1,3-glucan wet cake comprising; (i) heating an enzyme reaction solution comprising an aqueous basic buffered solution of *S. salivarius* gtfJ enzyme, sucrose and, optionally, antimicrobial agent to make a slurry containing poly alpha-1,3-glucan; (ii) filtering the slurry to isolate the poly alpha-1,3-glucan in the form of a wet cake; and (iii) washing the wet cake with water; (b) preparing a mixture from the wet cake with wood pulp, water and, optionally, plasticizers, tougheners and/or fibrillar strengthening agents; (c) homogenizing the mixture; (d) removing at least a portion of the water to form a flowable or malleable material; (e) forming the flowable or malleable material into a shape; and (f) drying the shape to form a solid article.

The present disclosure is still further directed toward a solid article prepared from a process comprising: (a) preparing a poly alpha-1,3-glucan wet cake comprising; (i) heating an enzyme reaction solution comprising an aqueous basic buffered solution of *S. salivarius* gtfJ enzyme, sucrose and, optionally, an antimicrobial agent to make a slurry containing poly alpha-1,3-glucan; (ii) filtering the slurry to isolate the poly alpha-1,3-glucan in the form of a wet cake; and (iii) washing the wet cake with water; (b) preparing a mixture from the wet cake with wood pulp, water and, optionally, plasticizers, tougheners and/or fibrillar strengthening agents; (c) homogenizing the mixture; (d) removing at least a portion of the water to form a flowable or malleable material; (e) forming the flowable or malleable material into a shape; and (f) drying the shape to form a solid article.

Test Methods

Bend Test measures the reduced brittleness of a flat sample. In this test, a flat sample is placed on the table and folded by hand back on itself, so that the edge travels through a 180° arc. The sample is then picked up, un-folded back to its original position and then folded through another 180° arc along the same crease in the opposite direction. The number of 180° bends before the sample breaks is recorded.

Thickness measurements were made with a hand-held micrometer, are approximate and represent the range within the sample.

EXAMPLES

The disclosure is further defined in the following Examples. It should be understood that these Examples, while indicating certain preferred aspects of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various uses and conditions.

Preparation of a Colloidal Dispersion Comprising Poly Alpha-1,3-Glucan

U.S. Pat. No. 7,000,000 disclosed a polysaccharide fiber comprising hexose units wherein at least 50% of the hexose units within the polymer were linked via alpha-1,3-glycosidic linkages using an *Streptococcus salivarius* gtfJ enzyme. This enzyme utilizes sucrose as a substrate in a polymerization reaction producing poly alpha-1,3-glucan and fructose as end-products.

A slurry of poly alpha-1,3-glucan was prepared from an aqueous solution (0.5 L) containing *Streptococcus salivarius* gtfJ enzyme (100 unit/L) described in U.S. Patent Appl. Publ. No. 2013/0244288, which is incorporated herein by reference in its entirety, sucrose (100 g/L) obtained from OmniPur Sucrose (EM8550), potassium phosphate buffer (10 mM) obtained from Sigma Aldrich, and FERMA-SURE®, an antimicrobial agent, (100 ppm) obtained from DuPont adjusted to pH 5.5. The resulting enzyme reaction solution was maintained at 20-25° C. for 24 hours. A slurry was formed since the poly alpha-1,3-glucan synthesized in the reaction was aqueous insoluble. The poly alpha-1,3-glucan solids produced in the reaction were collected using a Buchner funnel fitted with a 325-mesh screen over 40 micrometer filter paper, forming the wet cake which contains about 60-80 wt % of water. The poly alpha-1,3-glucan wet cake is then resuspended in water using an Ika Ultra-Turrax® T25 digital disperser, typically at 8000 rpm for 5 min.

Examples of the disclosure demonstrating the use of glucan dispersions to make solid, plastic-like sheets, composites and laminates were made using the following materials:

Glucan wet cake (a dispersion of undissolved, solid glucan particles dispersed in water). In this work the glucan solids level was 26%. This polymer in this work had a DPw of 800.

Glycerol (99.7% purity, VWR International, LLC, Radnor, Pa.), added as a 10% solution with de-ionized water Wood pulp, Type 37758 Bleached Kraft Pulp from Weyerhaeuser Water, de-ionized Nonwoven for lamination/impregnation (DuPont SONTARA® Style 8642, hydro-entangled Lyocell staple fibers, 61 g/m$^2$ basis weight, 24 mesh, with openings of approximately 0.8 mm)

Woven fabric for lamination/impregnation (cotton, open-weave gauze, 30 g/m$^2$ basis weight, 2 mm×2 mm openings)

Other materials used in preparation include:

Filter paper: VWR Type Qualitative 417, (VWR International, LLC, Radnor, Pa.)

Adsorbent material used during pressing: WypAll Brand L40 paper wipes, 30 g/m$^2$ basis weight (Kimberly Clark Corporation, Irving, Tex.)

The first step in the process of making these objects was to make a blend of ingredients that primarily contains undissolved glucan particles but can also include plasticizers, tougheners and fibrillar strengthening agents. This blend was made with a wide range of consistencies so that it could be coated, impregnated, molded, laminated or simply solidified.

Blend-Making Procedure

Samples of glucan dispersion containing various levels of additives were made according to the following procedure. Glucan wet cake, wood pulp, glycerol, water and/or other ingredients were mixed together in proportions as indicated in the table below. Ingredients were added to a vessel, starting with 30 g of glucan wet cake. Other ingredients were added as percentages of this value, as indicated. After adding all of the weighed ingredients, the volume was brought up to 400 ml by adding additional water.

The mixture was then homogenized for one minute at 12,000 rpm using an IKA ULTRA-TURRAX® T25 digital disperser (IKA-Works, Inc., Wilmington, N.C., USA; IKA, Staufen, Germany). The homogenizer was then cleaned to remove any wood pulp or glucan stuck in the blades. Any removed material was blended back into the batch and homogenized for two additional minutes at 13,400 rpm. The dispersion was then poured into a vacuum filter, a glass frit covered with the indicated filter paper, and hooked to vacuum (25 Torr). Water was pulled through the filter for two hours, leaving a malleable material on top of the filter. This filtration could be operated for less time to remove less water to make a lower viscosity coating, paste or putty.

Formation of Objects

Examples (E) 1-5 and
Comparative Examples (CE) 1-3

In process 1 (see Table 1), portions of this malleable material (made in the procedure above) were then pressed between layers of paper towels to remove and adsorb the water. To do this, the malleable material was spread evenly into one KC WypAll paper wipe, and covered with another paper wipe on top. This sandwich was then put between three more layers of wipes on top and three more on the bottom. This layered structure was then placed in a hydraulic press. It was pressed at 65° C. and 5,0000 psi for 15 minutes using a Carver laboratory hydraulic press (Carver, Inc., Wabash, Ind.). The sample was then removed from the press and placed in a 60° C. oven (held flat with a light weight on top) for three hours to dry. Optionally, the samples could be dried at a higher temperature (110° C.) to make a stiffer (and potentially less water-sensitive) product.

Examples (E) 6-8

In process 2 (see Table 2), portions of the malleable material were placed on both sides of a porous nonwoven fabric and on both sides of an open cotton woven fabric. These laminates and composites were pressed with the Carver press with 4 layers of wipes on each side using the same procedure as above.

TABLE 1

Process 1 Example Compositions and Results

| | Composition | | | Results | |
|---|---|---|---|---|---|
| Example | Glycerol (as % of glucan solids) | Wood pulp (as % of glucan solids) | Sample thickness (microns) | Blend Test (Number of Bends before breaking) | Observations |
| CE1 | 0 | 0 | 500-800 | 0 | Very brittle, bending not possible |
| CE2 | 30 | 0 | 500-800 | 0 | Very brittle, bending not possible |
| CE3 | 30 | 5 | 300-500 | 0 | Slightly more flexible, but no significant bending is possible |
| E1 | 30 | 15 | 500-1000 | 3-6 | |
| E2 | 30 | 25 | 500-1000 | >20 | |
| E3 | 30 | 50 | 1100-1700 | Very strong, could not be bent in Bend Test | Pulp was not well dispersed in this procedure |
| E4 | 0 | 15 | 600-1000 | NA | |
| E5 | 60 | 15 | 600-1000 | NA | Felt more flexible than Ex 4 |

Comparative Example 4

A free-flowing glucan powder with a DPw of 800 was dried further in a vacuum oven overnight at 60° C. to reach a glucan content of over 99%. The glucan dry powder was then blended with water and re-dried. The glucan again had the same powdery consistency that it started with. It did not form a solid article.

What is claimed is:

1. A solid article comprising:
   (a) from 50 to 90% by wt. poly alpha-1,3-glucan; and
   (b) from 10 to 50% by wt. wood pulp.

2. The solid article of claim 1, further comprising: plasticizers, tougheners and/or fibrillar strengthening agents.

3. The solid article of claim 2, wherein the plasticizer is glycerol.

4. The solid article of claim 1, in the form of sheets, composites, laminates and molded parts.

5. A process for making a solid article comprising:
   (a) preparing a poly alpha-1,3-glucan wet cake comprising;
      (i) heating an enzyme reaction solution comprising an aqueous basic buffered solution of *S. salivarius* gtfJ enzyme, sucrose and, optionally, antimicrobial agent to make a slurry containing poly alpha-1,3-glucan;
      (ii) filtering the slurry to isolate the poly alpha-1,3-glucan in the form of a wet cake; and
      (iii) washing the wet cake with water;
   (b) preparing a mixture from the wet cake with wood pulp, water and, optionally, plasticizers, tougheners and/or fibrillar strengthening agents;
   (c) homogenizing the mixture;
   (d) removing some water to form a flowable or malleable material;

TABLE 2

Process 2 Example Compositions and Results

| | Composition | | | Results | | |
|---|---|---|---|---|---|---|
| Example | Glycerol (as % of glucan solids) | Wood pulp (as % of glucan solids) | Other component (blended, coated or laminated) | Sample thickness (microns) | Blend Test (Number of Bends before breaking) | Observations |
| E6 | 30 | 15 | Nonwoven | 1100-1400 | >20 | Hard to bend, cannot tear by hand |
| E7 | 30 | 25 | Nonwoven | 1100-1400 | | Surface layer cracks when bent, but could not be torn or broken in tensile by hand |
| E8 | 30 | 25 | Woven | 1100-1600 | | Surface layer cracks when bent, but could not be torn or broken in tensile by hand |

(e) forming the flowable or malleable material into a shape; and
(f) drying the shape to form a solid article.

6. A solid article prepared according to claim 5.

\* \* \* \* \*